United States Patent

Cereda et al.

Patent Number: 4,643,993
Date of Patent: Feb. 17, 1987

[54] SUBSTITUTED HETEROCYCLYL-PHENYL-(SULFONYL-OR PHOSPHONYL)-AMIDINES

[75] Inventors: Enzo Cereda, Tortona; Arturo Donetti; Antonio Giachetti, both of Milano; Piero del Soldato, Monza, all of Italy

[73] Assignee: Istituto de Angeli S.p.A., Milan, Italy

[21] Appl. No.: 495,717

[22] Filed: May 18, 1983

[30] Foreign Application Priority Data

Jul. 29, 1982 [IT] Italy .............................. 22637 A/82

[51] Int. Cl.[4] .................. A61K 31/41; A61K 31/675; C07D 249/08; C07F 9/65
[52] U.S. Cl. ........................................ 514/93; 514/94; 514/383; 514/400; 514/406; 548/119; 548/269; 548/346; 548/373
[58] Field of Search ............... 548/119, 269, 346, 373; 514/93, 94, 383, 400, 406

[56] References Cited

U.S. PATENT DOCUMENTS 4,386,099  5/1983  Coreda et al. .................. 548/346 X
4,548,944  10/1985  Bietti et al. .......................... 514/363

Primary Examiner—Richard L. Raymond
Attorney, Agent, or Firm—Hammond & Littell, Weissenberger & Dippert

[57] ABSTRACT

Compounds of the formula

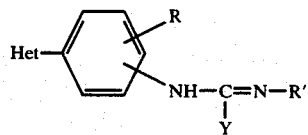

wherein
Het is a heterocycle containing 2 to 3 nitrogen atoms;
R is hydrogen, lower alkyl, alkoxy of 1 to 3 carbon atoms or halogen;
Y is —SO$_3$H or

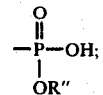

R″ is alkyl of 1 to 3 carbon atoms; and
R′ is straight or branched alkyl which may contain a heteroatom such as sulfur, oxygen or nitrogen; straight or branched alkenyl; cycloalkyl; alkylcycloalkyl; aryl; or aralkyl optionally substituted by lower alkyl, alkoxy of 1 to 3 carbon atoms or halogen; tautomers thereof, and non-toxic, pharmacologically acceptable acid addition salts thereof. The compounds as well as their salts are useful as anti-ulcerogenics and gastric acid secretion inhibitors.

9 Claims, No Drawings

SUBSTITUTED HETEROCYCLYL-PHENYL-(SULFONYL-OR PHOSPHONYL)-AMIDINES

This invention relates to novel substituted heterocyclyl-phenyl-(sulfonyl or phosphonyl)-amides and non-toxic acid addition salts thereof, to a method of preparing these compounds, to pharmaceutical compositions containing them as active ingredients, and to methods of using them as anti-ulcerogenics and gastric acid secretion inhibitors.

BACKGROUND OF THE INVENTION AND THE PRIOR ART

It is known that classic antihistamines, such as mepyramine, are capable of antagonizing some effects of histamine mediated by $H_1$-receptors. However, these compounds have no effect on gastric acid secretion which is instead affected by other antihistaminic agents defined by Black et al. (Nature 236, 385, 1972) as histamine $H_2$-receptor antagonists. This has indicated that another kind of receptors ($H_2$) already recognized by Ash and Shild (Brit. J. Pharmacol. Chem. Ther., 27, 427–439, 1966) is involved in the gastric secretory response which is not blocked by the conventional antihistamines of the $H_1$-type.

Examples of $H_2$-receptor antagonists capable of antagonizing gastric acid secretion include burimamide, metiamide, and cimetidine. The clinical efficacy of the latter as a gastric antisecretory agent stimulated a search for agents with higher potency, longer duration of action, and lesser side effects.

Recently, new $H_2$-antagonists such as ranitidine (Bradshaw et al., Brit. J. Pharmacol. 66, 464P, 1979), tiotidine (P. O. Jellin, Life Sci. 25, 2001, 1979) and BL 6341 (Cavanagh et al., Fed. Proc., 40, 2652, 1981) have been described.

In a structural sense these compounds resemble cimetidine, since they contain a substituted heterocycle joined by a methylthioethyl side chain to a "urea equivalent" neutral polar group.

In copending U.S. applications Ser. No. 322,903, filed Nov. 19, 1981, now U.S. Pat. No. 4,386,099, and 465,572, filed Feb. 10, 1983, now U.S. Pat. No. 4,548,944, we have described new classes of histamine $H_2$-antagonists, namely heterocyclyl-phenyl-formamidines, which are potent $H_2$-blockers and active antagonists of gastric acid secretion. These compounds do not resemble the so far known $H_2$-antagonists, such as cimetidine, ranitidine, etc., and are characterized by a phenylformamidine grouping bearing variously substituted heterocyclic rings.

DESCRIPTION OF THE INVENTION

More particularly, the present invention relates to a novel class of heterocyclyl-phenyl-(sulfonyl or phosphonyl)-amidines represented by the formula

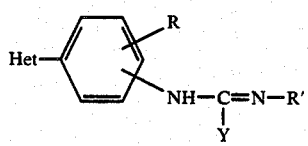

(I)

wherein
Het is a heterocycle containing 2 to 3 nitrogen atoms;
R is hydrogen, lower alkyl, alkoxy of 1 to 3 carbon atoms or halogen;
Y is -SO$_3$H or

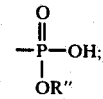

R'' is alkyl of 1 to 3 carbon atoms; and
R' is straight or branched alkyl which may contain a heteroatom such as sulfur, oxygen or nitrogen; straight or branched alkenyl; cycloalkyl; alkylcycloalkyl; aryl; or aralkyl optionally substituted by lower alkyl, alkoxy of 1 to 3 carbon atoms or halogen; tautomers thereof, and non-toxic, pharmacologically acceptable acid addition salts thereof.

It should be understood that although the double bond in the amidine radical has been inserted in a particular position, other tautomeric forms are possible, and that various tautomeric forms are also possible in the heterocyclic ring. It should also be understood that the sulfonyl- or phosphonylamidine radical may be in its zwitterionic form. The present invention includes such tautomeric forms within its scope, both in terms of the compounds of the invention and in terms of the method of preparation.

When Het in formula I represents a heterocyclic ring containing from 2 to 3 nitrogen atoms, this may be an unsaturated five-membered ring, such as the imidazole, triazole or pyrazole ring; when R represents a halogen atom, it may be a chlorine atom; when R' represents a straight or branched alkyl group, it may be an alkyl group containing from 1 to 8 carbon atoms which may contain an oxygen atom such as hydroxypropyl, hydroxybutyl or methoxypropyl, a sulfur atom, such as methylthioethyl or ethylthioethyl, or a nitrogen atom such as cyanoethyl; when R' represents a straight or branched alkenyl group, it may be alkenyl of 3 to 5 carbon atoms; when R' represents a cycloalkyl or alkylcycloalkyl group, it may contain from 3 to 7 carbon atoms; when R' represents an aryl or aralkyl group, the aromatic ring is phenyl, optionally substituted by a lower alkyl or alkoxy group containing from 1 to 3 carbon atoms, or by a halogen atom which may be a chlorine atom.

In formula I the sulfonyl- or phosphonyl-amidine radical may be in the ortho-, meta- or para-position on the benzene ring with respect to the Het group, and the group R may be in any position of the benzene ring.

A preferred subgenus is constituted by those compounds of the formula I wherein the sulfonyl- or phosphonylamidine radical is in the para-position with respect to the Het group on the phenyl ring,
Het is 2-imidazolyl, 4-imidazolyl, 3-pyrazolyl or 3-(1,2,4-triazolyl);
R is hydrogen, methyl, methoxy or chlorine;
Y is -SO$_3$H or

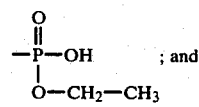

; and

R' is straight or branched alkyl of 3 to 5 carbon atoms or straight or branched alkenyl of 3 to 5 carbon atoms, each optionally containing an oxygen or sulfur atom or a cyano group; and non-toxic, pharmacologically acceptable acid addition salts thereof.

The compounds embraced by formula I may, for example, be prepared by reacting a heterocyclyl-phenylamine of the formula

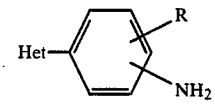   (II)

wherein Het and R have the meanings previously defined, with a compound of the formula

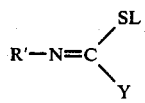   (III)

wherein

R' and Y the meanings previously defined, and
L is alkyl of 1 to 3 carbon atoms, such as methyl.

The reaction is generally carried out at a temperature of 0° to 60° C., preferably at room temperature, in the presence of a polar inert organic solvent such as dioxane or acetonitrile.

The compounds of the formula III in which Y is a sulfonic acid group can be prepared by known methods, for example by reacting an alkali metal thioxomethane-sulfonate of the formula

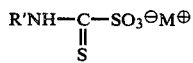   (IV)

in which R' has the meanings previously defined, and M is an alkali metal such as sodium or potassium, with an organic alkyl iodide or dimethyl sulfate in refluxing acetonitrile.

The compounds of the formula III wherein Y is a phosphonic acid monoalkyl ester can also be prepared by known methods, for example by reacting a thiocarbamoyl phosphonate of the formula

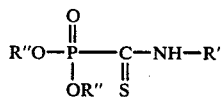   (V)

wherein R' and R" have the meanings previously defined, with an organic iodide of the formula LI, where L has the meanings previously defined, for instance with methyliodide, in the presence or absence of a polar inert solvent such as dioxane or acetonitrile.

The compounds of the formula I prepared according to the above process can be converted with organic or inorganic acids into non-toxic, pharmacologically acceptable acid addition salts, for example by conventional methods such as by reacting the compounds as bases with a solution of the corresponding acid in a suitable solvent. Particularly preferred acids are, for example, hydrochloric, sulfuric, maleic or fumaric acid. The salts thus obtained are generally soluble in water.

The following examples illustrate the present invention and will enable others skilled in the art to understand it more completely. It should be understood, however, that the invention is not limited sohely to the particular examples given below.

PREPARATION OF STARTING COMPOUNDS OF THE FORMULA III

EXAMPLE 1

1-Methylthio-1-isopropylimino-methanesulfonate

The title compound was prepared according to the method of W. Walter and C. Rohloff [Liebigs Ann. Chem. 491 (1977)] by refluxing for two hours a solution of 1-isopropylamino-1-thioxo-sodium methanesulfonate (30.8 g) and dimethylsulfate (37.8 g) in acetonitrile (650 ml). The compound which precipitated on standing was collected by filtration to give a white solid. M.p. 155° C. (dec.).

The following compounds were prepared in analogous manner:

1-Methylthio-1-ethylimino-methanesulfonate. White solid. M.p. 148°–149° C.

1-Methylthio-1-allylimino-methanesulfonate. Waxy solid.

1-Methylthio-1-methylthioethylimino-methanesulfonate. Thick oil.

EXAMPLE 2

S-Methyl-N-Isopropyl-thioimidoyl-phosphonic acid monoethyl ester

A solution of diethyl N-isopropyl-thiocarbamoyl phosphonate (11 g), prepared according to V. A. Petrov and A. A. Neimysheva, Zhur. Obsch. Khimii, 29, 1819 (1959), and methyliodide (48 ml) was refluxed for two hours and then evaporated to dryness. By crystallizing the crude residue from acetonitrile and diethyl ether, the title compound was obtained as a white solid. M.p. 94°–97° C. (dec.).

In analogous manner the following intermediates were also produced:

S-Methyl-N-ethyl-thioimidoyl-phosphonic acid monoethyl ester. Thick oil.

S-Methyl-N-methyl-thioethylthioimidoyl-phosphonic acid monoethyl ester. Thick reddish oil.

PREPARATION OF END PRODUCTS OF THE FORMULA I

EXAMPLE 3

N-Isopropyl-N'-[4-(imidazol-4-yl)-phenyl]-amidino-sulfonic acid

A solution of 1-methylthio-1-isopropylimino-methanesulfonate (6.8 g) in acetonitrile (150 ml) was added slowly to a solution of 4-(4-amino phenyl)-1-H-imidazole (5 g) in acetonitrile (250 ml) at room temperature. The reaction mixture was stirred overnight, and the product which crystallized out was collected by filtration to give the crude title compound, which was purified via its maleate in 95% ethanol. M.p. 209° C. (dec.).

Analysis: $C_{17}H_{20}N_4O_7S$; Found %: C-47.87; H-4.82; N-13.11; Calc. %: C-48.10; H-4.75; N-13.20.

EXAMPLE 4

N-Allyl-N'-[4-(imidazol-4-yl)-phenyl]-amidino-sulfonic acid

A solution of 1-methylthio-1-allyl-imino-methanesulfonate (6.13 g) in acetonitrile (50 ml) was added slowly to a suspension of 4-(4-amino-phenyl)-1-H-imidazole (5 g) in acetonitrile (60 ml). The reaction mixture was stirred for two days at room temperature, cooled and filtered. The crude title compound was purified via its maleate in 95% ethanol. M.p. 183°–184° C.

Analysis: $C_{17}H_{18}N_4O_7S$; Found %: C-47.92; H-4.36; N-13.17; Calc. %: C-48.34; H-4.29; N-13.26.

EXAMPLE 5

N-Ethyl-N'-[4-(imidazol-4-yl)-phenyl]-amidino-sulfonic acid

A solution of 1-methylthio-1-ethyl-imino-methanesulfonate (0.7 g) in acetonitrile (10 ml) was added dropwise to a suspension of 4 (4-amino-phenyl)-1-H-imidazole monohydrochloride (0.6 g) in acetonitrile (30 ml). The reaction mixture was stirred for three days at room temperature, and then the white solid still in suspension was collected by filtration. This crude product was triturated with methanol to give the title compound as its hydrochloride. M.p. 198°–200° C. (dec.).

Analysis: $C_{12}H_{15}N_4SO_3Cl$; Found %: C-43.51; H-4.62; N-16.85; Calc. %: C-43.57; H-4.57; N-16.94.

EXAMPLE 6

By utilizing the suitable 1-methylthio-1-substituted imino-methane-sulfonates, all prepared according to Example 1, and substitution of the following phenylamines:

(a) 4-(3-methyl-4-amino-phenyl)-1-H-imidazole,
(b) 4-(3-methoxy-4-amino-phenyl)-1-H-imidazole,
(c) 4-(3-chloro-4-amino-phenyl)-1-H-imidazole
(d) 4-(3-amino-phenyl)-1-H-imidazole,
(e) 2-(4-amino-phenyl)1-H-imidazole,
(f) 3-(4-amino-phenyl)-pyrazole, or
(g) 2-(4-amino-phenyl)-1,2,4-triazole
for the 4-(4-amino-phenyl)-1-H-imidazole in the procedures of Examples 3, 4 and 5, led to the production of the following compounds:

N-Methylthioethyl-N'-[4-(imidazol-4-yl)-phenyl]-amidino-sulfonic acid,
N-Methoxyethyl-N'-[4-(imidazol-4-yl)-phenyl]-amidino-sulfonic acid,
N-Cyanoethyl-N'-[4-(imidazol-4-yl)-phenyl]-amidino-sulfonic acid,
N-n-Octyl-N'-[4-(imidazol-4-yl)-phenyl]-amidino-sulfonic acid,
N-Cyclohexyl-N'-[4-(imidazol-4-yl)-phenyl]-amidino-sulfonic acid,
N-4-Chlorophenyl-N'-[4-(imidazol-4-yl)-phenyl]-amidino-sulfonic acid,
N-Benzyl-N'-[4-(imidazol-4-yl)-phenyl]-amidino-sulfonic acid,
N-Ethylthioethyl-N'-[4-(imidazol-4-yl)-2-methyl-phenyl]-amidino-sulfonic acid,
N-n-Butyl-N'-[4-(imidazol-4-yl)-2-methoxy-phenyl]-amidino-sulfonic acid,
N-3-Methyl-but-2-enyl-N'-[4-(imidazol-4-yl)-2-chloro-phenyl]-amidino sulfonic acid,
N-Isopropyl-N'-[3-(imidazol-4-yl)-phenyl]-amidino-sulfonic acid,
N-Cyclopropylmethyl-N'-[4-(imidazol-2-yl)-phenyl]-amidino-sulfonic acid,
N-Phenyl-N'-[4-(pyrazol-3-yl)-phenyl]-amidino-sulfonic acid, and
N-Methoxyethyl-N'-[4-(1,2,4--triazol-3-yl)-phenyl]-amidino-sulfonic acid.

EXAMPLE 7

N-Isopropyl-N'-[4-(imidazol-4-yl)-phenyl]-amidino-phosphonic acid monoethyl ester A solution of 4-(4-amino-phenyl)-1-H-imidazole (3.85 g) and S-methyl-N-isopropyl-thioimidoyl-phosphonic acid monoethyl ester (6 g) in acetonitrile (140 ml) was stirred overnight at room temperature. The solid product which separated out was filtered off and recrystalized from water and acetone to give the title compound as a base. M.p. 235° C.

Analysis: $C_{15}H_{21}N_4O_3P$; Found %: C-53.07; H-6.19; N-16.47; Calc. %: C-53.56; H-6.29; N-16.66.

EXAMPLE 8

N-Methylthioethyl-N'-[4-(imidazol-4-yl)-phenyl]-amidino-phosphonic acid monoethyl ester A solution of 4-(4-amino phenyl)-1-H-imidazole (5 g) and S-methyl-N-methylthioethyl-thioimidoyl-phosphonic acid monoethyl ester (8.1 g) in acetonitrile (200 ml) was stirred overnight at room temperature. The solid product which separated out on standing was filtered off and recrystallized from acetone to give the title compound as a base. M.p. 240°–241° C.

Analysis: $C_{13}H_{21}N_4O_3PS$; Found %: C-45.16; H-6.17; N-16.12; Calc. %: C-45.38; H-6.15; N-16.27.

EXAMPLE 9

By utilizing the suitable S-methyl-thioimidoylphosphonic acid monoethyl ester and substituting the following phenylamines:

(a) 4-(3-methyl-4-amino-phenyl)-1-H-imidazole,
(b) 4-(3-methoxy-4-amino-phenyl)-1-H-imidazole,
(c) 4-(3-chloro-4-amino-phenyl)-1-H-imidazole,
(d) 4-(3-amino-phenyl)-1-H-imidazole,
(e) 2-(4-amino-phenyl)-1-H-imidazole,
(f) 3-(4-amino-phenyl)-pyrazole, or
(g) 3-(4-amino-phenyl)-1,2,4-triazole
for 4-(4-amino-phenyl)-1-H-imidazole in the procedure of Example 7 or 8, the following monoethyl esters were obtained:

N-Benzyl-N'-[4-(imidazol-4-yl)-phenyl]-amidinophosphonic acid monoethyl ester,
N-3-Methoxy phenyl-N'-[4-(imidazol-4-yl)-phenyl]-amidino-phosphonic acid monoethyl ester,
N-Cyclopropylmethyl-N'-[4-(imidazol-4-yl)-phenyl]-amidino-phosphonic acid monoethyl ester,
N-Allyl-N'-[4-(imidazol-4-yl)-phenyl]-amidino-phosphonic acid monoethyl ester,
N-n-Octyl-N'-[4-(imidazol-4-yl) phenyl]-amidino-phosphonic acid monoethyl ester,
N-Cyanoethyl-N'-[4-(imidazol-4-yl)-phenyl]-amidino-phosphonic acid monoethyl ester,
N-Methylthioethyl-N'-[4-(imidazol-4-yl)-2-methyl-phenyl]-amidino-phosphonic acid monoethyl ester,
N-Methoxyethyl-N'-[4-(imidazol-4-yl)-2-chloro-phenyl]-amidino-phosphonic acid monoethyl ester,
N-Isopropyl-N'-[4-(imidazol-4-yl)2-methoxy-phenyl]-amidino-phosphonic acid monoethyl ester, N-Cyclohexyl-N'-[3-(imidazol-4-yl)-phenyl]-amidino-phosphonic acid monoethyl ester,
N-Cyanoethyl-N'-[4-(imidazol-2-yl)-phenyl]-amidino-phosphonic acid monoethyl ester,
N-Phenyl-N'-[4-(pyrazol-3-yl)-phenyl]-amidino-phosphonic acid monoethyl ester, and N-3-Methyl-but-2-enyl-N'-[4-(1,2,4-triazol-3-yl)-phenyl]-amidino-phosphonic acid monoethyl ester.

The compounds of the present invention, that is, those embraced by formula I, their tautomers and non-toxic, pharmacologically acceptable acid addition salts thereof, have useful pharmacodynamic properties. More particularly, they exhibit anti-ulcerogenic and gastric acid secretion inhibiting activities in warm-blooded animals such as rats.

The compounds of the present invention do not possess antihistamine ($H_2$) activity per se, since they were found to be inactive in the in vitro assays usually employed for $H_2$-antagonist activity (for example, inhibition of the positive chronotropic effect of histamine in isolated guinea pig atria).

However, the compounds show antihistamine ($H_2$) activity when administered by oral route to rats. To demonstrate their in vivo antihistamine effect, rats were used in which activation of the histamine ($H_2$) receptors in the gastrointestinal tract by the specific agonist dimaprit (100 mg/kg i.v.) causes the appearance of severe gastric lesions [P. Del Soldato, Pharmacol. Res. Comm. 14, 175 (1982)]. The test compounds were administered to female fasted (24 hours) Sprague-Dawley rats at variable intervals prior the challenge with dimaprit. The gastric lesions were evaluated 60 minutes after the injection of the agonist.

The protection against ulcers by means of the test compounds, expressed as a percentage of animals with no signs of gastric damage, indicates antihistamine ($H_2$) activity.

The results of a typical experiment concerning the classic $H_2$-antagonist cimetidine and two of the compounds of the present invention are shown in the following table:

| Compound of Example | Dose mg/kg p.o. | Dimaprit-Induced Gastric Ulcer % Protection at | |
|---|---|---|---|
| | | 1 hr | 6 hrs |
| 3 | 1 | 30 | 40 |
| | 3 | 30 | 70 |
| 7 | 1 | 30 | 50 |
| | 3 | 40 | 60 |
| CIMETIDINE | 20 | 80 | 0 |
| | 80 | 100 | 10 |

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds according to the present invention is from 1.42 to 7.14 mgm/kg body weight, preferably 0.71 to 3.57 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 10

Tablets

The tablet composition is compounded from the following ingredients:

| | |
|---|---|
| N—Isopropyl-N'—[4-(imidazol-4-yl)-phenyl]-amidino-sulfonic acid maleate | 150 parts |
| Lactose | 250 parts |
| Corn starch | 30 parts |
| Magnesium stearate | 3 parts |
| Total | 433 parts |

Preparation

The active ingredient, the lactose and the corn starch are mixed and homogeneously moistened with water. After screening of the moist mass and drying in a tray driver, the mixture is again passed through a screen, and magnesium stearate is added. Then, the mixture is compressed into tablets weighing 433 mg each. Each tablet contains 150 mg of the active ingredient.

EXAMPLE 11

Capsules

The capsule filler composition is compounded from the following ingredients:

| | |
|---|---|
| N—Isopropyl-N'—[4-(imidazol-4-yl)-phenyl]-amidino-phosphonic acid monoethyl ester | 150 parts |
| Corn starch | 50 parts |
| Magnesium stearate | 2 parts |
| Total | 202 parts |

Preparation

The active ingredient is mixed with the excipients, and the mixture is passed through a screen and mixed homogeneously in a suitable device. The resulting mixture is filled into hard gelation capsules (202 mg per capsule); each capsule contains 150 mg of the active ingredient

EXAMPLE 12

The solution is compounded from the following ingredients:

| | |
|---|---|
| N—Ethyl-N'—[4-(imidazol-4-yl)-phenyl]-amidino-sulfonic acid hydrochloride | 150 parts |
| Sterile water | 5000 parts by vol. |

Preparation

The active ingredient is dissolved in the sterile water, and the resulting solution is filled into 5-cc ampules under sterile conditions. Each ampule contains mg of the active ingredient.

Any one of the other compounds embraced by formula I or a non-toxic, pharmacologically acceptable acid addition salt thereof may be substituted for the particular active ingredient in Examples 10 through 12. Likewise, the amount of active ingredient in these illustrative examples may be varied to achieve the dosage unit range set forth above, and the amounts and nature

We claim:

1. A compound of the formula

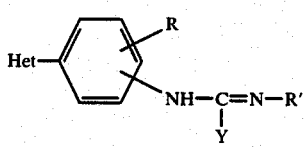

wherein

Het is imidazolyl, triazolyl or pyrazolyl;
R is hydrogen, lower alkyl, alkoxy of 1 to 3 carbon atoms or halogen;
Y is -SO₃H or

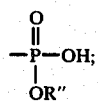

R" is alkyl of 1 to 3 carbon atoms; and
R' is straight or branched alkyl which may contain a sulfur, oxygen or nitrogen heteroatom; straight or branched alkenyl; cycloalkyl; alkyl-cycloalkyl; aryl optionally substituted by lower alkyl, alkoxy of 1 to 3 carbon atoms or halogen; or aralkyl optionally substituted by lower alkyl, alkoxy of 1 to 3 carbon atoms or halogen; a tautomer thereof, or a non-toxic, pharmacologically acceptable acid addition salt thereof.

2. A compound of claim 1, where the acid addition salt is the hydrochloride, maleate, sulfate or fumarate.

3. A compound of claim 1, where amidine radical is in the para-position on the benzene ring with respect to the Het group.

4. A compound of claim 3,
where
Het is 2-imidazolyl, 4-imidazolyl, 3-pyrazolyl or 3-(1,2,4-triazolyl);
R is hydrogen, methyl, methoxy or chlorine;
Y is -SO₃H or

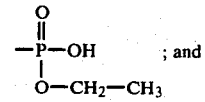 ; and

R' is straight or branched alkyl of 3 to 5 carbon atoms or straight or branched alkenyl of 3 to 5 carbon atoms, each optionally containing an oxygen or sulfur atom or a cyano group;
or a non-toxic, pharmacologically acceptable acid addition salt thereof.

5. A compound of claim 4, where the acid addition salt is the maleate, hydrochloride, sulfate or fumarate.

6. A compound of claim 1, which is N-isopropyl-N'-[4-(imidazol-4-yl)-phenyl]-amidino-sulfonic acid or a non-toxic, pharmacologically acceptable acid addition salt thereof.

7. A compound of claim 1, which is N-isopropyl-N'-[4-(imidazol-4-yl)-phenyl]-amidino-phosphonic acid or a non-toxic, pharmacologically acceptable acid addition salt thereof.

8. An anti-ulcerogenic and gastric acid secretion inhibiting pharmaceutical composition consisting essentially of an inert pharmaceutical carrier and an effective anti-ulcerogenic and gastric acid secretion inhibiting amount of a compound of claim 1.

9. The method of treating gastric ulcers and inhibiting gastric acid secretion in a warm-blooded animal in need thereof, which comprises perorally or parenterally administering to said animal an effective anti-ulcerogenic and gastric acid secretion inhibiting amount of a compound of claim 1.

* * * * *

UNITED STATES PATENT AND TRADEMARK OFFICE
CERTIFICATE OF CORRECTION

PATENT NO. : 4,643,993

DATED : February 17, 1987

INVENTOR(S) : ENZO CEREDA ET AL.

It is certified that error appears in the above-identified patent and that said Letters Patent is hereby corrected as shown below:

Column 1, line 7: "amides" should read -- amidines --.

Column 3, line 23: "Y the" should read --Y have the --.

Column 8, line 60: "contains mg" should read -- contains 150 mg --.

Signed and Sealed this

Eighteenth Day of August, 1987

Attest:

DONALD J. QUIGG

*Attesting Officer*     *Commissioner of Patents and Trademarks*